(12) United States Patent
Wu

(10) Patent No.: US 12,377,216 B1
(45) Date of Patent: Aug. 5, 2025

(54) MEDICAMENT DELIVERY DEVICE

(71) Applicant: Genzyme Corporation, Cambridge, MA (US)

(72) Inventor: Haiming Wu, Weston, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 18/990,326

(22) Filed: Dec. 20, 2024

(51) Int. Cl.
*A61M 5/20* (2006.01)
*A61M 5/315* (2006.01)
*A61M 5/32* (2006.01)

(52) U.S. Cl.
CPC .......... *A61M 5/20* (2013.01); *A61M 5/31511* (2013.01); *A61M 5/31525* (2013.01); *A61M 5/3202* (2013.01); *A61M 2005/2006* (2013.01); *A61M 2202/0007* (2013.01); *A61M 2205/3317* (2013.01); *A61M 2205/3327* (2013.01); *A61M 2205/3379* (2013.01); *A61M 2205/50* (2013.01)

(58) Field of Classification Search
CPC ................ A61M 5/20; A61M 5/31511; A61M 2005/2006; A61M 2205/3317
See application file for complete search history.

(56) References Cited

U.S. PATENT DOCUMENTS

| | | | | |
|---|---|---|---|---|
| RE35,979 E | * | 12/1998 | Reilly | ................ A61M 5/31511 600/432 |
| 2008/0154202 A1 | * | 6/2008 | Nemoto | ................... G05G 7/10 604/154 |
| 2011/0306937 A1 | * | 12/2011 | Andreoni | ............ A61M 5/3257 604/198 |

OTHER PUBLICATIONS

Needle-based injection systems for medical use requirements and test methods, Part 1: Needle injection systems, ISO 11608 1:2014(E), Third Edition, Switzerland, ISO, Dec. 15, 2014, pp. 1-13.

* cited by examiner

*Primary Examiner* — Bradley J Osinski
(74) *Attorney, Agent, or Firm* — Fish & Richardson P.C.

(57) ABSTRACT

A medicament delivery device for injecting a medicament is described. The medicament delivery device comprises a housing having a proximal end and a distal end, the housing being configured to receive a medicament container. A plunger is moveable in a longitudinal direction within the housing for dispensing medicament from the medicament container when the medicament container is received within the housing. A plunger drive magnet is operatively coupled to the housing, and the plunger drive magnet is configured to provide a magnetic field. A component is configured to magnetically interact with the magnetic field of the plunger drive magnet so as to cause a force to be exerted on the plunger for causing the plunger to move in the longitudinal direction.

19 Claims, 3 Drawing Sheets

MEDICAMENT DELIVERY DEVICE

TECHNICAL FIELD

The present disclosure relates to a medicament delivery device and to a method of using a medicament delivery device.

BACKGROUND

Medicament delivery devices, such as auto-injectors, are known in the art for dispensing medicament to an injection site of a patient.

Some medicament delivery devices comprise a compression spring to move or apply a force to various components of the medicament delivery device in use, for example to bias a plunger, which may also be referred to in the technical field as a piston, of the device in a distal direction for dispensing medicament from the device. Some medicament delivery devices may comprise a compression spring to bias a needle shield of the device into a covered position thereof in which the needle shield covers a needle of the device. Such compression springs are typically held under compression prior to usage and therefore components of the device are exposed to stresses resulting from the long-term compression of the compression spring which may lead to creep, e.g. plastic creep, in materials of the device, thereby affecting the performance of the device. Furthermore, the maximum force able to be provided by such compression springs is limited, for example due to size constraints of the device or due to material property constraints on components of the device. Thus, for devices comprising such compression springs as a plunger bias, limitations are set on the maximum viscosity of medicament contained in the medicament delivery device. Furthermore, the force provided by such compression springs may be difficult to control.

SUMMARY

The present disclosure relates to an improved or alternative means of driving a plunger of a medicament delivery device.

According to an aspect of the present disclosure, there is provided a medicament delivery device for injecting medicament, wherein the medicament delivery device comprises:
- a housing having a proximal end and a distal end, the housing being configured to receive a medicament container;
- a plunger moveable in a longitudinal direction within the housing for dispensing medicament from the medicament container when the medicament container is received within the housing;
- a plunger drive magnet operatively coupled to the housing, the plunger drive magnet being configured to provide a magnetic field; and
- a component configured to magnetically interact with the magnetic field of the plunger drive magnet so as to cause a force to be exerted on the plunger for causing the plunger to move in the longitudinal direction.

Thus, a non-contact medicament delivery device may be provided in which the plunger drive does not directly contact the plunger.

In some embodiments, the component is operatively coupled (e.g. affixed or attached) to the plunger.

In some embodiments, the component is in abutting engagement with the plunger.

In some embodiments, the component is a ferromagnetic component.

In some embodiments, the component is made of or comprises a ferromagnetic material.

In some embodiments, the component is a plunger bias configured to bias the plunger in the longitudinal direction.

In some embodiments, the plunger bias comprises a compression spring.

In some embodiments, the plunger is or comprises the component.

In some embodiments, the medicament delivery device comprises a plunger rod, wherein the plunger rod is or comprises the component.

In some embodiments, the component is a plunger bias magnet operatively coupled to the plunger bias, wherein the plunger bias magnet is configured to provide a magnetic field configured to magnetically interact with the magnetic field of the plunger drive magnet so as to cause a force to be exerted on the plunger for causing the plunger to move in the longitudinal direction. In some embodiments, the plunger bias magnet comprises a permanent magnet.

In some embodiments, the component is a plunger magnet operatively coupled to the plunger, wherein the plunger magnet is configured to provide a magnetic field configured to magnetically interact with the magnetic field of the plunger drive magnet so as to cause a force to be exerted on the plunger for causing the plunger to move in the longitudinal direction. In some embodiments, the plunger magnet comprises a permanent magnet.

In some embodiments, the medicament delivery device comprises a plunger rod and wherein the component is a plunger rod magnet operatively coupled to the plunger rod, wherein the plunger rod magnet is configured to provide a magnetic field configured to magnetically interact with the magnetic field of the plunger drive magnet so as to cause a force to be exerted on the plunger for causing the plunger to move in the longitudinal direction. In some embodiments, the plunger rod magnet comprises a permanent magnet.

In some embodiments, the plunger rod is in abutting engagement with the plunger.

In some embodiments, the plunger rod comprises the plunger rod magnet at a proximal end of the plunger rod.

In some embodiments, the housing is elongate.

In some embodiments, the longitudinal direction extends between the distal end and the proximal end of the housing.

In some embodiments, the force exerted on the plunger causes the plunger to move in a distal direction for dispensing medicament from the medicament container when the medicament container is received within the housing.

In some embodiments, the plunger drive magnet is affixed or attached to the housing.

In some embodiments, the plunger drive magnet comprises a permanent magnet.

In some embodiments, the plunger drive magnet comprises an electromagnet.

In some embodiments, the electromagnet of the plunger drive magnet comprises an energizable coil.

In some embodiments, the energizable coil is energizable to provide the magnetic field of the plunger drive magnet.

In some embodiments, the energizable coil of the plunger drive magnet is arranged to extend peripherally around the medicament container when the medicament container is received within the housing.

In some embodiments, the electromagnet of the plunger drive magnet comprises a plurality of independently energizable and/or adjacently arranged energizable coils.

In some embodiments, the plurality of energizable coils are arranged along a longitudinal direction of the housing.

In some embodiments, the medicament delivery device comprises an electrical energy source configured to provide electrical energy to the electromagnet of the plunger drive magnet for energising the electromagnet of the plunger drive magnet so as to provide the magnetic field of the plunger drive magnet.

In some embodiments, the medicament delivery device comprises a controller configured to control the electromagnet of the plunger drive magnet so as to control the force (e.g. a magnitude thereof) exerted on the plunger.

In some embodiments, the controller is configured to control the electromagnet of the plunger drive magnet so as to control the movement of the plunger in the longitudinal direction.

In some embodiments, the controller is configured to control the magnetic field (e.g. an intensity thereof) of the plunger drive magnet so as to control the force (e.g. a magnitude thereof) exerted on the plunger.

In some embodiments, the controller is configured to control the magnetic field (e.g. an intensity thereof) of the plunger drive magnet so as to control the movement of the plunger in the longitudinal direction.

In some embodiments, the controller is configured to independently control (e.g. selectively energise) one or more of the plurality of energizable coils so as to control the force (e.g. a magnitude thereof) exerted on the plunger and/or the movement of the plunger in the longitudinal direction.

In some embodiments, the controller is configured to independently control (e.g. selectively energise) one or more of the plurality of energizable coils so as to independently control a magnetic field (e.g. an intensity thereof) provided by the plurality of energizable coils so as to control the force (e.g. a magnitude thereof) exerted on the plunger and/or the movement of the plunger in the longitudinal direction.

In some embodiments, the controller is configured to control the electromagnet of the plunger drive magnet so as to control a rate of movement (e.g. speed or velocity) of the plunger in the longitudinal direction.

In some embodiments, the controller is configured to control the electromagnet of the plunger drive magnet so as to control a rate of movement (e.g. speed or velocity) of the plunger in the longitudinal direction so as to control a rate at which medicament is dispensed from the medicament container when received within the housing.

In some embodiments, the medicament delivery device comprises a magnetic field sensor configured to provide a signal associated with the component.

In some embodiments, the signal is associated with a magnetic field of the component.

In some embodiments, the signal is indicative of the longitudinal position of the component within the housing.

In some embodiments, the signal is indicative of the longitudinal position of the plunger within the housing.

In some embodiments, the signal is indicative of a rate of movement of the component in the longitudinal direction.

In some embodiments, the signal is indicative of a rate of movement of the plunger in the longitudinal direction.

In some embodiments, the signal is indicative of the magnetic field intensity of the plunger magnet.

In some embodiments, the signal is indicative of the magnetic field intensity of the plunger rod magnet.

In some embodiments, the signal is indicative of the magnetic field intensity of the plunger bias magnet.

In some embodiments, the magnetic field sensor comprises a Hall Effect sensor.

In some embodiments, the medicament delivery device comprises a processor configured to determine one or more of a longitudinal position of the plunger within the housing, a rate of movement (e.g. speed or velocity) of the plunger in the longitudinal direction within the housing, a rate at which medicament is dispensed from the medicament container, and/or a quantity of medicament dispensed from the medicament container, based on the signal provided by the magnetic field sensor. In some embodiments, the processor is configured to determine the quantity of medicament dispensed from the medicament container based on the determined rate of movement (e.g. speed or velocity) of the plunger in the longitudinal direction within the housing.

In some embodiments, the medicament delivery device comprises a controller configured to control the electromagnet of the plunger drive magnet so as to control the longitudinal position of the plunger within the housing based on the determined longitudinal position of the plunger within the housing, the determined rate of movement of the plunger in the longitudinal direction within the housing, the determined rate at which medicament is dispensed from the medicament container, and/or the determined quantity of medicament dispensed from the medicament container.

In some embodiments, the controller is configured to control the electromagnet of the plunger drive magnet so as to control the force (e.g. a magnitude thereof) exerted on the plunger based on the determined longitudinal position of the plunger within the housing, the determined rate of movement (e.g. speed or velocity) of the plunger in the longitudinal direction within the housing, the determined rate at which medicament is dispensed from the medicament container, and/or the determined quantity of medicament dispensed from the medicament container.

In some embodiments, the controller is configured to individually control one or more of the plurality of energizable coils of the electromagnet of the plunger drive magnet based on the determined longitudinal position of the plunger within the housing, the determined rate of movement of the plunger in the longitudinal direction within the housing, the determined rate at which medicament is dispensed from the medicament container, and/or the determined quantity of medicament dispensed from the medicament container, so as to control the force (e.g. a magnitude thereof) exerted on the plunger and/or the movement of the plunger in the longitudinal direction.

In some embodiments, the controller is configured to individually control a magnetic field intensity of a magnetic field provided by one or more of the plurality of energizable coils of the plunger drive magnet based on the determined longitudinal position of the plunger within the housing, the determined rate of movement of the plunger in the longitudinal direction within the housing, the determined rate at which medicament is dispensed from the medicament container, and/or the determined quantity of medicament dispensed from the medicament container, so as to control the force (e.g. a magnitude thereof) exerted on the plunger and/or the movement of the plunger in the longitudinal direction.

In some embodiments, the medicament delivery device comprises a needle shield configured to be movable between an extended position for covering a needle of the medicament container when the medicament container is received within the housing and a retracted position for exposing the needle for injection, e.g. from a distal end of the device.

In some embodiments, the needle shield is configured to be movable in a proximal direction of the housing from the extended position to the retracted position, the needle shield being biased in a distal direction towards the extended position by a needle shield extension force. In some embodiments, the needle shield is configured to be movable in a proximal direction of the housing from the extended position to the retracted position.

In some embodiments, the plunger drive magnet comprises an electromagnet and wherein the medicament delivery device comprises a switch configured to energise the electromagnet of the plunger drive magnet so as to provide the magnetic field of the plunger drive magnet upon movement of the needle shield from the extended position towards the retracted position.

In some embodiments, the component is a first component, wherein the medicament delivery device further comprises a second component, the second component being configured to magnetically interact with the magnetic field of the plunger drive magnet so as to cause a force to be exerted on the second component, the force exerted on the second component acting in a proximal direction so as to reduce the needle shield extension force.

In some embodiments, the second component is operatively coupled (e.g. attached or affixed) to the needle shield.

In some embodiments, the second component is in abutting engagement with the needle shield.

In some embodiments, the second component is a ferromagnetic component.

In some embodiments, the second component is made of or comprises a ferromagnetic material.

In some embodiments, the second component comprises a permanent magnet.

In some embodiments, the second component is a needle shield bias configured to provide the needle shield extension force. In some embodiments, the needle shield bias comprises a compression spring.

In some embodiments, the medicament delivery device comprises a needle shield bias configured to bias the needle shield towards the extended position and thereby provide the needle shield extension force.

In some embodiments, the second component is or comprises the needle shield.

In some embodiments, the second component is a needle shield magnet operatively coupled to the needle shield, the needle shield magnet being configured to provide a magnetic field and wherein the magnetic field of the needle shield magnet is configured to magnetically interact with the magnetic field of the plunger drive magnet so as to cause a force to be exerted on the needle shield, the force acting in a proximal direction so as to reduce the needle shield extension force.

In some embodiments, the second component is a needle shield magnet operatively coupled, e.g. affixed or attached, to the needle shield, the needle shield magnet being configured to provide a magnetic field and wherein the magnetic field of the needle shield magnet is configured to magnetically interact with the magnetic field of the plunger drive magnet so as to cause a force to be exerted on the needle shield so as to cause the needle shield to be retained in the retracted position against the needle shield extension force.

In some embodiments, the medicament delivery device further comprises a needle shield retraction magnet configured to provide a magnetic field configured to magnetically interact with the second component so as to cause a force to be exerted on the second component, the force exerted on the second component acting in a proximal direction so as to reduce the needle shield extension force.

In some embodiments, the medicament delivery device further comprises a needle shield retraction magnet configured to provide a magnetic field configured to magnetically interact with the second component so as to cause a force to be exerted on the second component so as to cause the needle shield to be retained in the retracted position against the needle shield extension force.

In some embodiments, the second component is a needle shield magnet operatively coupled, e.g. affixed or attached, to the needle shield, the needle shield magnet being configured to provide a magnetic field and wherein the medicament delivery device further comprises a needle shield retraction magnet configured to provide a magnetic field configured to magnetically interact with the magnetic field of the needle shield magnet so as to cause a force to be exerted on the needle shield, the force acting in a proximal direction so as to reduce the needle shield extension force.

In some embodiments, the second component is a needle shield magnet operatively coupled, e.g. affixed or attached, to the needle shield, the needle shield magnet being configured to provide a magnetic field and wherein the medicament delivery device further comprises a needle shield retraction magnet configured to provide a magnetic field configured to magnetically interact with the magnetic field of the needle shield magnet so as to cause a force to be exerted on the needle shield so as to cause the needle shield to be retained in the retracted position against the needle shield extension force.

In some embodiments, the needle shield retraction magnet is coupled, e.g. affixed or attached, to the housing.

In some embodiments, the needle shield retraction magnet comprises a permanent magnet.

In some embodiments, the needle shield retraction magnet comprises an electromagnet.

In some embodiments, the electromagnet of the needle shield retraction magnet comprises an energizable coil energizable to provide the magnetic field of the needle shield retraction magnet.

In some embodiments, the controller is configured to control the electromagnet of the needle shield retraction magnet so as to control the needle shield extension force (e.g. a magnitude thereof) based on the determined longitudinal position of the plunger within the housing, the determined rate of movement of the plunger in the longitudinal direction within the housing, the determined rate at which medicament is dispensed from the medicament container, and/or the determined quantity of medicament dispensed from the medicament container In some embodiments, the medicament delivery device comprises an electrical energy source configured to provide electrical energy to the electromagnet of the needle shield retraction magnet for energising the electromagnet of the needle shield retraction magnet.

In some embodiments, the medicament delivery device comprises a switch configured to actuate upon movement of the needle shield from the extended position towards the retracted position. In some embodiments, the switch is configured to energise the electromagnet of the plunger drive magnet upon movement of the needle shield from the extended position towards the retracted position.

In some embodiments, the medicament delivery device comprises a module configured to be detachably attachable to the housing.

In some embodiments, the module comprises the plunger drive magnet.

In some embodiments, the module comprises the controller.

In some embodiments, the module comprises the processor.

In some embodiments, the module comprises the electrical energy source.

In some embodiments, the module comprises the switch.

In some embodiments, the module comprises the needle shield retraction magnet.

In some embodiments, the medicament delivery device comprises a switch configured to energise the electromagnet of the needle shield retraction magnet upon movement of the needle shield from the extended position towards the retracted position.

In some embodiments, the medicament container contains medicament.

According to another aspect of the present disclosure, there is provided a method of using a medicament delivery device for injecting medicament, the medicament delivery device comprising:
- a housing having a proximal end and a distal end, the housing being configured to receive a medicament container;
- a plunger moveable in a longitudinal direction within the housing for dispensing medicament from the medicament container when the medicament container is received within the housing;
- a plunger drive magnet operatively coupled to the housing, the plunger drive magnet being configured to provide a magnetic field; and
- a component configured to magnetically interact with the magnetic field of the plunger drive magnet;
- the method comprising the step of:
- causing the component to magnetically interact with the magnetic field of the plunger drive magnet so as to cause a force to be exerted on the plunger for causing the plunger to move in the longitudinal direction.

In some embodiments, the plunger drive magnet comprises an electromagnet, and the method comprises the further step of energising the electromagnet of the plunger drive magnet so as to provide the magnetic field.

In some embodiments, the component is a first component and wherein the medicament delivery device further comprises:
- a needle shield configured to be movable between an extended position for covering a needle of the medicament container when the medicament container is received within the housing and a retracted position for exposing the needle for injection, e.g. from a distal end of the device, the needle shield being configured to be movable in a proximal direction of the housing from the extended position to the retracted position, the needle shield being biased in a distal direction towards the extended position by a needle shield extension force;
- a needle shield retraction magnet comprising an electromagnet configured to provide a magnetic field configured to magnetically interact with a second component so as to cause a force to be exerted on the second component, the force acting in a proximal direction so as to reduce the needle shield extension force; and
- a switch configured to energise the electromagnet of the needle shield retraction magnet upon movement of the needle shield from the extended position towards the retracted position;
- wherein the method comprises the step of:
- moving the needle shield from the extended position towards the retracted position so as to actuate the switch to thereby cause the electromagnet of the needle shield retraction magnet to become energised so as to provide the magnetic field of the needle shield retraction magnet and thereby cause a force to be exerted on the second component, the force acting in a proximal direction so as to reduce the needle shield extension force.

In some embodiments, the second component is a needle shield bias configured to provide the needle shield extension force.

In some embodiments, the second component is or comprises the needle shield.

In some embodiments, the second component is a needle shield magnet operatively coupled to the needle shield, the needle shield magnet being configured to provide a magnetic field and wherein the magnetic field of the needle shield magnet is configured to magnetically interact with the magnetic field of the plunger drive magnet so as to cause a force to be exerted on the needle shield, the force acting in a proximal direction so as to reduce the needle shield extension force.

In some embodiments, the plunger drive magnet comprises an electromagnet, wherein the medicament delivery device comprises:
- a needle shield configured to be movable between an extended position for covering a needle of the medicament container when the medicament container is received within the housing and a retracted position for exposing the needle for injection, e.g. from a distal end of the device; and
- a switch configured to energise the electromagnet of the plunger drive magnet so as to provide the magnetic field of the plunger drive magnet upon movement of the needle shield from the extended position towards the retracted position;
- wherein the method comprises the step of:
- moving the needle shield from the extended position towards the retracted position so as to actuate the switch to thereby cause the electromagnet of the plunger drive magnet to become energised so as to provide the magnetic field of the plunger drive magnet and thereby cause a force to be exerted on the plunger for causing the plunger to move in the longitudinal direction.

In some embodiments, the plunger drive magnet comprises an electromagnet, the medicament delivery device comprising a controller configured to control the electromagnet of the plunger drive magnet so as to control the movement of the plunger in the longitudinal direction;
the method comprising the further step of:
controlling the electromagnet of the plunger drive magnet so as to control the movement of the plunger in the longitudinal direction.

In some embodiments, the plunger drive magnet comprises an electromagnet, the medicament delivery device comprising a controller configured to control the electromagnet of the plunger drive magnet so as to control the force (e.g. a magnitude thereof) exerted on the plunger;
the method comprising the further step of:
controlling the electromagnet of the plunger drive magnet so as to control the force (e.g. a magnitude thereof) exerted on the plunger.

In some embodiments, the plunger drive magnet comprises an electromagnet, and wherein the medicament delivery device comprises:
- a magnetic field sensor configured to provide a signal associated with the component;
- a processor configured to determine one or more of a longitudinal position of the plunger within the housing, a rate of movement (e.g. speed or velocity) of the plunger in the longitudinal direction within the housing, a rate at which medicament is dispensed from the medicament container, and/or a quantity of medicament dispensed from the medicament container, based on the signal provided by the magnetic field sensor; and a controller configured to control the electromagnet of the plunger drive magnet so as to control the longitudinal position of the plunger within the housing based on the determined longitudinal position of the plunger within the housing, the determined rate of movement of the plunger within the housing in the longitudinal direction, the determined rate at which medicament is dispensed from the medicament container, and/or the determined quantity of medicament dispensed from the medicament container;

the method comprising the further step of:

receiving a signal associated with the component from the magnetic field sensor;

determining one or more of a longitudinal position of the plunger within the housing, a rate of movement (e.g. speed or velocity) of the plunger in the longitudinal direction within the housing, a rate at which medicament is dispensed from the medicament container, and/or a quantity of medicament dispensed from the medicament container, based on the received signal; and controlling the electromagnet of the plunger drive magnet based on the determined longitudinal position of the plunger within the housing, the determined rate of movement of the plunger in the longitudinal direction within the housing, the determined rate at which medicament is dispensed from the medicament container, and/or the determined quantity of medicament dispensed from the medicament container so as to control the movement of the plunger with respect to the medicament container.

In some embodiments, the plunger drive magnet comprises an electromagnet, and wherein the medicament delivery device comprises:

a magnetic field sensor configured to provide a signal associated with the component;

a processor configured to determine one or more of a longitudinal position of the plunger within the housing, a rate of movement (e.g. speed or velocity) of the plunger in the longitudinal direction within the housing, a rate at which medicament is dispensed from the medicament container, and/or a quantity of medicament dispensed from the medicament container, based on the signal provided by the magnetic field sensor; and a controller configured to control the electromagnet of the plunger drive magnet so as to control the force (e.g. a magnitude thereof) exerted on the plunger based on the determined longitudinal position of the plunger within the housing, the determined rate of movement of the plunger within the housing in the longitudinal direction, the determined rate at which medicament is dispensed from the medicament container, and/or the determined quantity of medicament dispensed from the medicament container;

the method comprising the further step of:

receiving a signal associated with the component from the magnetic field sensor;

determining one or more of a longitudinal position of the plunger within the housing, a rate of movement (e.g. speed or velocity) of the plunger in the longitudinal direction within the housing, a rate at which medicament is dispensed from the medicament container, and/or a quantity of medicament dispensed from the medicament container, based on the received signal; and controlling the electromagnet of the plunger drive magnet based on the determined longitudinal position of the plunger within the housing, the determined rate of movement of the plunger in the longitudinal direction within the housing, the determined rate at which medicament is dispensed from the medicament container, and/or the determined quantity of medicament dispensed from the medicament container so as to control the force (e.g. a magnitude thereof) exerted on the plunger.

In some embodiments, the method comprises the further step of controlling the electromagnet of the plunger drive magnet based on the determined longitudinal position of the plunger within the housing, the determined rate of movement of the plunger in the longitudinal direction within the housing, or the determined rate at which medicament is dispensed from the medicament container, so as to provide a substantially constant rate at which medicament is dispensed from the medicament container.

In some embodiments, the method comprises the further step of controlling the electromagnet of the plunger drive magnet based on the determined quantity of medicament dispensed from the medicament container so as to cause a predetermined quantity of medicament to be dispensed from the medicament container.

According to another aspect of the present disclosure, there is provided a medicament delivery device for injecting medicament, wherein the medicament delivery device comprises:

a housing having a proximal end and a distal end, the housing being configured to receive a medicament container comprising a needle;

a needle shield configured to be movable between an extended position for covering the needle of the medicament container when the medicament container is received within the housing and a retracted position for exposing the needle for injection, the needle shield being configured to be movable in a proximal direction of the housing from the extended position to the retracted position, the needle shield being biased in a distal direction towards the extended position by a needle shield extension force;

a needle shield retraction magnet operatively coupled to the housing, the needle shield retraction magnet being configured to provide a magnetic field; and a component configured to magnetically interact with the magnetic field of the needle shield retraction magnet so as to cause a force to be exerted on the component, the force acting in a proximal direction so as to reduce the needle shield extension force. In some embodiments, the component is operatively coupled to the needle shield.

In some embodiments, the needle shield is configured to be movable in a proximal direction of the housing from the extended position to the retracted position.

In some embodiments, the needle shield is provided at a distal end of the housing.

In some embodiments, the magnetic interaction of the magnetic field of the needle shield retraction magnet with the component causes the needle shield to be retained in the retracted position against the needle shield extension force.

In some embodiments, the component is operatively coupled, e.g. affixed or attached, to the needle shield.

In some embodiments, the component is a ferromagnetic component.

In some embodiments, the component is made from or comprises a ferromagnetic material.

In some embodiments, the component comprises a permanent magnet.

In some embodiments, the component is a needle shield bias configured to provide the needle shield extension force. In some embodiments, the needle shield bias comprises a compression spring.

In some embodiments, the medicament delivery device comprises a needle shield bias configured to bias the needle shield towards the extended position and thereby provide the needle shield extension force.

In some embodiments, the component is or comprises the needle shield.

In some embodiments, the component is a needle shield magnet operatively coupled, e.g. affixed or attached to, to the needle shield, the needle shield magnet being configured to provide a magnetic field and wherein the magnetic field of the needle shield magnet is configured to magnetically interact with the magnetic field of the needle shield retraction magnet so as to cause a force to be exerted on the needle shield, the force acting in a proximal direction so as to reduce the needle shield extension force.

In some embodiments, the component is a needle shield magnet operatively coupled, e.g. affixed or attached, to the needle shield, the needle shield magnet being configured to provide a magnetic field and wherein the magnetic field of the needle shield magnet is configured to magnetically interact with the magnetic field of the needle shield retraction magnet so as to cause a force to be exerted on the needle shield so as to cause the needle shield to be retained in the retracted position against the needle shield extension force.

In some embodiments, the magnetic interaction of the component with the magnetic field of the needle shield retraction magnet causes the needle shield to be retained in the retracted position against the needle shield extension force.

In some embodiments the needle shield retraction magnet is coupled, e.g. affixed or attached, to the housing.

In some embodiments, the needle shield magnet and/or the needle shield retraction magnet comprises a permanent magnet.

In some embodiments, the needle shield retraction magnet comprises an electromagnet.

In some embodiments, the electromagnet of the needle shield retraction magnet comprises an energizable coil energizable to provide the magnetic field of the needle shield retraction magnet.

In some embodiments, the energizable coil is arranged so as to extend peripherally around the needle shield.

In some embodiments, the medicament delivery device comprises an electrical energy source configured to provide electrical energy to the electromagnet of the needle shield retraction magnet for energising the electromagnet of the needle shield retraction magnet so as to provide the magnetic field of the needle shield retraction magnet.

In some embodiments, the medicament delivery device comprises a switch configured to energise the electromagnet of the needle shield retraction magnet so as to provide the magnetic field of the needle shield retraction magnet upon movement of the needle shield from the extended position towards the retracted position.

In some embodiments, the medicament delivery device further comprises:

a plunger moveable in a longitudinal direction within the housing for dispensing medicament from the medicament container when the medicament container is received within the housing;

a magnetic field sensor configured to provide a signal associated with the component;

a processor configured to determine a longitudinal position of the plunger within the housing, a rate of movement (e.g. speed or velocity) of the plunger within the housing in the longitudinal direction, a rate at which medicament is dispensed from the medicament container, and/or a quantity of medicament dispensed from the medicament container, based on the signal provided by the magnetic field sensor; and a controller configured to control the electromagnet of the needle shield retraction magnet so as to control the needle shield extension force (e.g. a magnitude thereof) based on the determined longitudinal position of the plunger within the housing, the determined rate of movement of the plunger in the longitudinal direction within the housing, the determined rate at which medicament is dispensed from the medicament container, and/or the determined quantity of medicament dispensed from the medicament container.

According to another aspect of the present disclosure, there is provided a method of using a medicament delivery device for injecting medicament, the medicament delivery device comprising:

a housing having a proximal end and a distal end, the housing being configured to receive a medicament container comprising a needle;

a needle shield configured to be movable between an extended position for covering the needle of the medicament container when the medicament container is received within the housing and a retracted position for exposing the needle for injection, the needle shield being configured to be movable in a proximal direction of the housing from the extended position to the retracted position, the needle shield being biased in a distal direction towards the extended position by a needle shield extension force;

a needle shield retraction magnet operatively coupled to the housing, the needle shield retraction magnet being configured to provide a magnetic field; and a component configured to magnetically interact with the magnetic field of the needle shield retraction magnet; and the method comprising the step of:

causing the component to magnetically interact with the magnetic field of the needle shield retraction magnet so as to cause a force to be exerted on the component, the force acting in a proximal direction so as to reduce the needle shield extension force.

In some embodiments, the needle shield retraction magnet comprises an electromagnet configured to provide the magnetic field of the needle shield retraction magnet;

the method comprising the step of:

energising the electromagnet of the needle shield retraction magnet so as to provide the magnetic field of the needle shield retraction magnet and thereby cause a force to be exerted on the component, the force acting in a proximal direction so as to reduce the needle shield extension force.

In some embodiments, the needle shield retraction magnet comprises an electromagnet configured to provide the magnetic field of the needle shield retraction magnet and the medicament delivery device further comprises a switch configured to energise the electromagnet of the needle shield retraction magnet upon movement of the needle shield from the extended position towards the retracted position;

the method comprising the step of:
moving the needle shield from the extended position towards the retracted position so as to cause the switch to energise the electromagnet of the needle shield retraction magnet so as to provide the magnetic field of the needle shield retraction magnet and thereby cause a force to be exerted on the component, the force acting in a proximal direction so as to reduce the needle shield extension force.

In some embodiments, the medicament delivery device further comprises:
a plunger moveable in a longitudinal direction within the housing for dispensing medicament from the medicament container when the medicament container is received within the housing;
a magnetic field sensor configured to provide a signal associated with the component;
a processor configured to determine a longitudinal position of the plunger within the housing, a rate of movement (e.g. speed or velocity) of the plunger within the housing in the longitudinal direction, a rate at which medicament is dispensed from the medicament container, and/or a quantity of medicament dispensed from the medicament container, based on the signal provided by the magnetic field sensor; and
a controller configured to control the electromagnet of the needle shield retraction magnet so as to control the needle shield extension force (e.g. a magnitude thereof) based on the determined longitudinal position of the plunger within the housing, the determined rate of movement of the plunger in the longitudinal direction within the housing, the determined rate at which medicament is dispensed from the medicament container, and/or the determined quantity of medicament dispensed from the medicament container;
the method comprising the steps of
receiving a signal associated with the component from the magnetic field sensor;
determining one or more of a longitudinal position of the plunger within the housing, a rate of movement (e.g. speed or velocity) of the plunger within the housing in the longitudinal direction, a rate at which medicament is dispensed from the medicament container, and/or a quantity of medicament dispensed from the medicament container, based on the received signal; and
controlling the electromagnet of the needle shield retraction magnet based on the determined longitudinal position of the plunger within the housing, the determined rate of movement of the plunger within the housing in the longitudinal direction, the determined rate at which medicament is dispensed from the medicament container, and/or the determined quantity of medicament dispensed from the medicament container so as to control the needle shield extension force (e.g. a magnitude thereof).

According to another aspect of the present disclosure, there is provided a module configured to be detachably attachable to a medicament delivery device for injecting medicament, the module comprising:
a plunger drive magnet configured to provide a magnetic field so as to cause a force to be exerted on a plunger of the medicament delivery device when the module is attached to the medicament delivery device for causing the plunger to move in a longitudinal direction of the medicament delivery device.

According to another aspect of the present disclosure, there is provided a module configured to be detachably attached to a medicament delivery device for injecting medicament, the module comprising:
a needle shield retraction magnet configured to provide a magnetic field configured to magnetically interact with a component of the medicament delivery device when the module is attached to the medicament delivery device so as to cause a force to be exerted on a needle shield of the medicament delivery device, the needle shield being configured to be movable between an extended position for covering a needle of the medicament container when a medicament container is received within the housing and a retracted position for exposing the needle for injection, the force acting in a direction towards the retracted position.

According to another aspect of the disclosure there is provided a kit of parts comprising:
a module configured to be detachably attachable to the housing of a medicament delivery device, the module comprising a plunger drive magnet configured to provide a magnetic field;
and
a medicament delivery for injecting medicament, the medicament delivery device comprising:
a housing having a proximal end and a distal end, the housing being configured to receive a medicament container;
a plunger moveable in a longitudinal direction within the housing for dispensing medicament from the medicament container when the medicament container is received within the housing; and
a component configured to magnetically interact with the magnetic field of the plunger drive magnet so as to cause a force to be exerted on the plunger for causing the plunger to move in the longitudinal direction.

According to another aspect of the disclosure there is provided a kit of parts comprising:
a module configured to be detachably attachable to the housing of a medicament delivery device, the module comprising a needle shield retraction magnet, the needle shield retraction magnet being configured to provide a magnetic field;
and
a medicament delivery for injecting medicament, the medicament delivery device comprising:
a housing having a proximal end and a distal end, the housing being configured to receive a medicament container comprising a needle;
a needle shield configured to be movable between an extended position for covering the needle of the medicament container when the medicament container is received within the housing and a retracted position for exposing the needle for injection, the needle shield being configured to be movable in a proximal direction of the housing from the extended position to the retracted position, the needle shield being biased in a distal direction towards the extended position by a needle shield extension force; and
a component configured to magnetically interact with the magnetic field of the needle shield retraction magnet of the module so as to cause a force to be exerted on the component, the force acting in a proximal direction so as to reduce the needle shield extension force.

According to another aspect of the present disclosure, there is provided a module configured to be detachably attachable to a medicament delivery device for injecting medicament, the module comprising:

a plunger drive magnet configured to provide a first magnetic field for causing a force to be exerted on a plunger of the medicament delivery device; and a needle shield retraction magnet configured to provide a second magnetic field for causing a needle shield extension force of a needle shield of the medicament delivery device to be reduced.

According to another aspect of the present disclosure, there is provided a method of manufacturing or assembling a medicament delivery device, wherein the medicament delivery device has the features of any of the medicament delivery devices described and/or contemplated herein.

According to another aspect of the present disclosure, there is provided a method of manufacturing or assembling a module, wherein the module has the features of any of the modules described and/or contemplated herein.

BRIEF DESCRIPTION OF THE DRAWINGS

Embodiments will now be described, by way of example only, with reference to the accompanying drawings, in which.

DETAILED DESCRIPTION

Figure 1A:
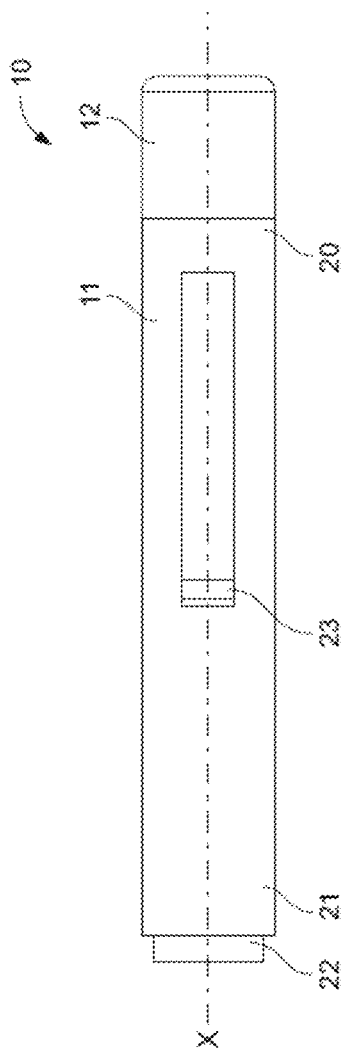
FIG. 1A is a schematic view of a medicament delivery device with a cap attached.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy.

One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1B:
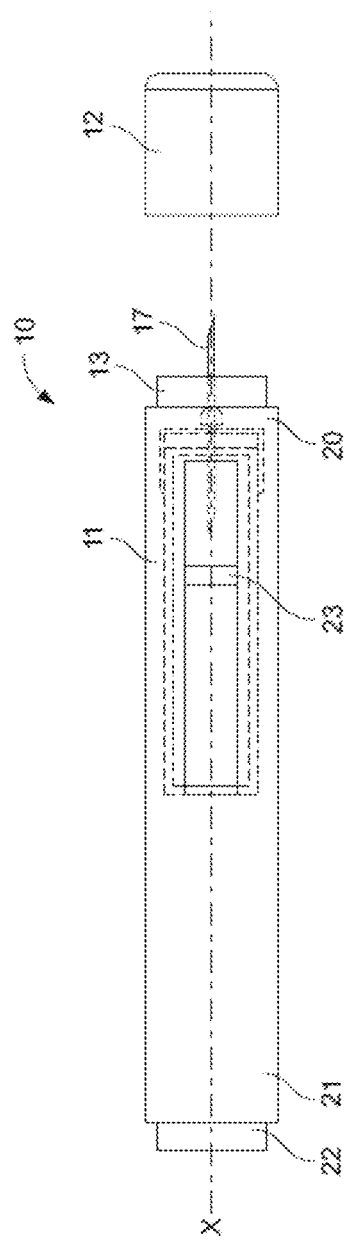
FIG. 1B is a schematic view of the medicament delivery device of FIG. 1A with the cap removed.

According to some embodiments of the present disclosure, an exemplary drug delivery device 10 is shown in FIGS. 1A & 1B. The device 10, as described above, is configured to inject a medicament into a patient's body. The device 10 includes a housing 11 which typically contains a reservoir containing the medicament to be injected (e.g., a syringe) and the components required to facilitate one or more steps of the delivery process. The device 10 can also include a cap assembly 12 that can be detachably mounted to the housing 11. A user typically removes the cap 12 from the housing 11 before device 10 is operated.

As shown, the housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

The device 10 can also include a needle sleeve 13 coupled to the housing 11 to permit movement of the sleeve 13 relative to the housing 11. For example, the sleeve 13 can move in a longitudinal direction parallel to longitudinal axis X. Specifically, movement of the in a proximal direction can permit a needle 17 to extend from a distal region 20 of housing 11.

Insertion of the needle 17 can occur via several mechanisms. For example, the needle 17 may be fixedly located relative to the housing 11 and initially be located within an extended needle sleeve 13. Proximal movement of sleeve 13 by placing a distal end of the sleeve 13 against a patient's body and moving the housing 11 in a distal direction will uncover the distal end of the needle 17. Such relative movement allows the distal end of the needle 17 to extend into the patient's body. Such insertion is termed "manual" insertion as the needle 17 is manually inserted via the patient's manual movement of the housing 11 relative to the sleeve 13.

Another form of insertion is "automated," whereby the needle 17 moves relative to the housing 11. Such insertion can be triggered by movement of the sleeve 13 or by another form of activation, for example, a button 22. As shown in FIGS. 1A & 1B, the button 22 is located at a proximal end of the housing 11. However, in other embodiments, button 22 could be located on a side of the housing 11.

Other manual or automated features can include drug injection or needle retraction, or both. Injection is the process by which a bung or piston 23 is moved from a proximal location within a syringe (not shown) to a more distal location within the syringe in order to force a medicament from the syringe through needle 17. In some embodiments, a drive spring (not shown) is under compression before device 10 is activated. A proximal end of the drive spring can be fixed within proximal region 21 of housing 11, and a distal end of the drive spring can be configured to apply a compressive force to a proximal surface of piston 23. Following activation, at least part of the energy stored in the drive spring can be applied to the proximal surface of piston 23. This compressive force can act on piston 23 to move it in a distal direction. Such distal movement acts to compress the liquid medicament within the syringe, forcing it out of needle 17.

Following injection, needle 17 can be retracted within the sleeve 13 or housing 11. Retraction can occur when the sleeve 13 moves distally as a user removes device 10 from a patient's body. This can occur as needle 17 remains fixedly located relative to housing 11. Once a distal end of the sleeve 13 has moved past a distal end of needle 17, and needle 17 is covered, the sleeve 13 can be locked. Such locking can include locking any proximal movement of the sleeve 13 relative to the housing 11.

Another form of needle retraction can occur if the needle 17 is moved relative to the housing 11. Such movement can occur if the syringe within the housing 11 is moved in a proximal direction relative to the housing 11. This proximal movement can be achieved by using a retraction spring (not shown), located in the distal region 20. A compressed retraction spring, when activated, can supply sufficient force to the syringe to move it in a proximal direction. Following sufficient retraction, any relative movement between the needle 17 and the housing 11 can be locked with a locking mechanism. In addition, the button 22 or other components of the device 10 can be locked as required.

Figures 2A, 2B:
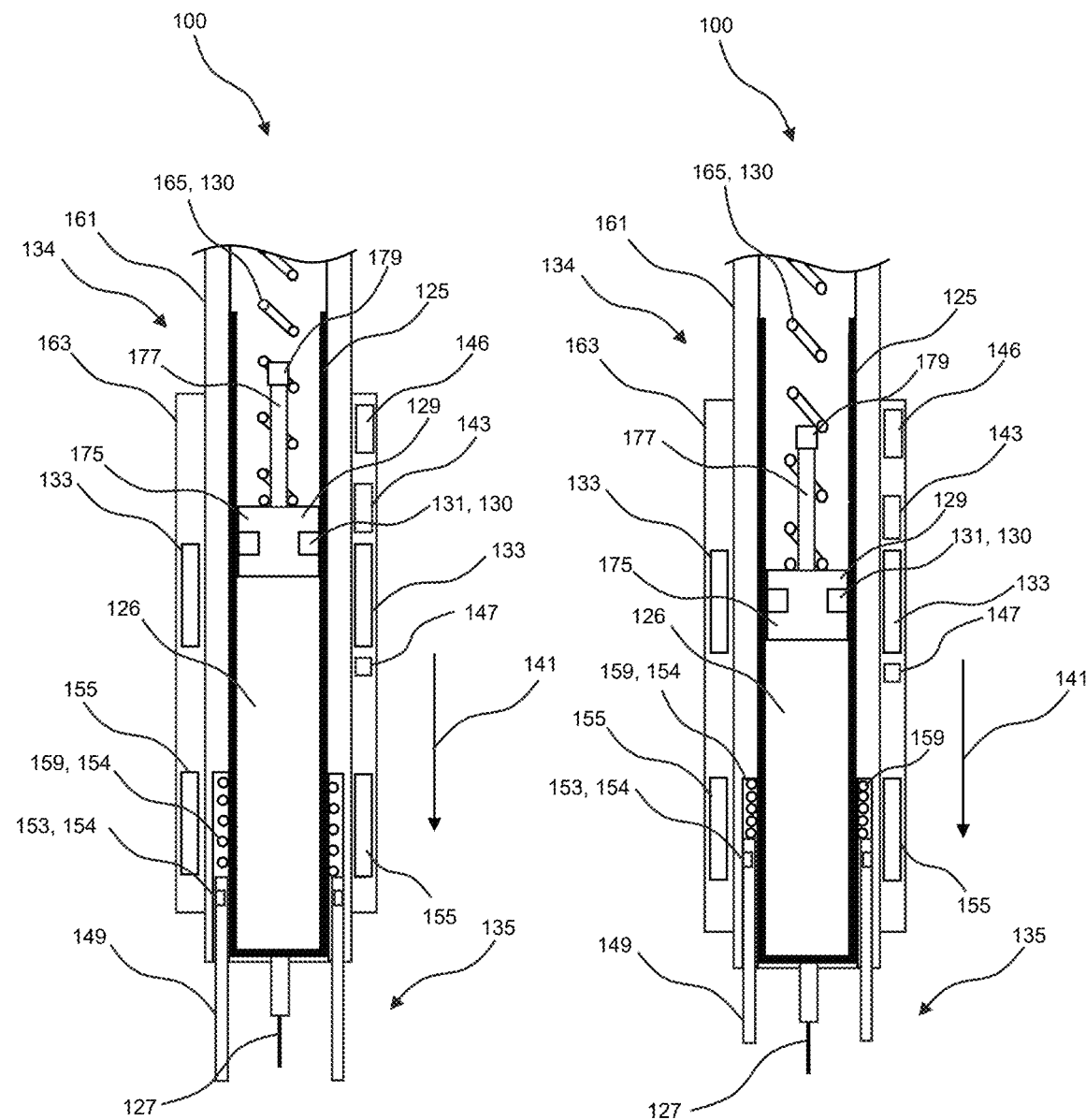
FIG. 2A is a schematic cross-sectional view of parts of another medicament delivery device, the medicament delivery device comprising a plunger drive magnet and a needle shield retraction magnet each comprising a permanent magnet, wherein a needle-shield of the medicament delivery device is in an extended position in which a needle of the medicament delivery device is covered.
FIG. 2B is a schematic cross-sectional view of parts of the medicament delivery device of FIG. 2A wherein the needle-shield is in a retracted position in which the needle is exposed for injection.

FIGS. 2A and 2B show a medicament delivery device 100 according to a further embodiment of the present disclosure. The medicament delivery device 100 of this example is an autoinjector.

The medicament delivery device 100 comprises an elongate body or housing 161 comprising a distal end 135 and an opposed proximal end 134. The housing 161 is configured to receive a medicament container 125 (which may in some embodiments be a syringe 125) for containing medicament 126. When a medicament container 125 is received within the housing 161, a needle of the medicament container 125 may be arranged at the distal end 135 of the housing 161. The needle 127 is in fluid communication with the medicament container 125 for dispensing the medicament 126 from the medicament container 125.

A plunger 129, or piston 129, is slidably and sealingly received within the medicament container 125 and moveable in a longitudinal direction 141 within the housing 161, the longitudinal direction extending between the distal end 136 and the proximal end 134 of the housing 161. A longitudinally extending plunger rod 177, arranged substantially parallel to a longitudinal direction 141 of the housing 161, is in abutting engagement with the plunger 129, although in some embodiments the plunger rod 177 may be integrally formed with the plunger 129. When the plunger 129 is caused to move distally, the plunger 129 applies a hydraulic force to the medicament 126 contained within the medicament container 125 and thereby forces the medicament 126 to be dispensed through the needle 127.

A plunger drive magnet 133 is operatively coupled or affixed to the housing 161 such that when the plunger 129 moves in the longitudinal direction 141 within the medicament container 125, the plunger 129 moves with respect to the plunger drive magnet 133. As shown in FIGS. 2A and 2B, the plunger drive magnet 133 of this embodiment is provided as a ring configured to extend circumferentially around the medicament container 125 such that the medicament container 125 is arranged within the annulus of the ring, although this is not essential and any suitable shape or configuration of the plunger drive magnet 133 may instead be used. In some embodiments a plurality of such plunger drive magnets 133 may be provided.

The plunger drive magnet 133 in this embodiment is a permanent magnet. In this embodiment the plunger drive magnet 133 is made from a ferromagnetic material although any other suitable magnetic material may instead be used. In other embodiments, such as those disclosed in respect of FIGS. 3A and 3B, the plunger drive magnet 133 may be an electromagnet.

The plunger drive magnet 133 is configured to provide a magnetic field which is configured to magnetically interact with a component 130 of the medicament delivery device so as to cause a force to be exerted on the plunger for causing the plunger to move longitudinally and within the medicament container 125 for causing medicament 126 to be dispensed from the medicament container 125 when the medicament container 125 is received within the housing 161.

In this embodiment, the magnetic interaction of the magnetic field of the plunger drive magnet 133 and the component 130 causes a force to be applied to the plunger 129 which causes the plunger to move distally within the medicament container 125 so as to dispense medicament from the medicament container 125 via the needle 127.

In some embodiments, the component 130 may be the plunger 129. For example, the plunger 129 may be a ferromagnetic plunger 129 in that the ferromagnetic plunger 129 may be made from or may comprise ferromagnetic material. Thus, the ferromagnetic plunger 129 may magnetically interact with the magnetic field provided by the plunger drive magnet 133 for causing a force to be applied to the plunger 129 for moving the plunger 129 in the longitudinal direction.

In other embodiments, the component 130 may be a plunger magnet 131 operatively coupled to the plunger 129. In this embodiment, the plunger magnet 131 is a permanent magnet. The plunger magnet 131 is configured to provide a magnetic field which is configured to magnetically interact with the magnetic field provided by the plunger drive magnet 133 for causing a force to be applied to the plunger 129 for moving the plunger 129 in the longitudinal direction.

In some embodiments, the plunger magnet 131 may be affixed to the plunger 129. In other embodiments, the plunger magnet 131 may not be affixed to the plunger 129, for example the plunger magnet 131 may be arranged in abutting engagement with the plunger 129 so as to engage the plunger 129 for causing the plunger 129 to move in the longitudinal direction 141. In this embodiment, the plunger magnet 131 is provided as an insert 131 affixed, e.g. adhered, to the plunger 129. As shown in FIGS. 2A and 2B, the plunger magnet 131 of this embodiment is provided as a ring 131 configured to extend circumferentially around the plunger 129, although this is not essential and any suitable shape or configuration of plunger magnet 131 may instead be used. In some embodiments a plurality of such plunger magnets 131 may be provided.

In other embodiments, the component 130 may be the plunger rod 177. For example, the plunger rod 177 may be a ferromagnetic plunger rod 177 in that ferromagnetic plunger rod 177 may be made from or may comprise ferromagnetic material. Thus, the ferromagnetic plunger rod 177 may be configured magnetically interact with the magnetic field provided by the plunger drive magnet 133 for causing a force to be applied to the plunger 129 for moving the plunger 129 in the longitudinal direction 141.

In other embodiments, the component 130 may be a plunger rod magnet 179 operatively coupled to the plunger rod 177, for example in some embodiments the plunger rod magnet 179 may be arranged, e.g. affixed to, a proximal end of the plunger rod 177.

In some embodiments, the plunger rod magnet 179 is a permanent magnet. The plunger rod magnet 179 is configured to provide a magnetic field which is configured to magnetically interact with the magnetic field provided by the plunger drive magnet 133 for causing a force to be applied to the plunger 129 for moving the plunger 129 in the longitudinal direction.

In some embodiments, the plunger rod magnet 179 may be affixed to the plunger rod 177. In other embodiments, the plunger rod magnet 179 may not be affixed to the plunger rod 177, for example the plunger rod magnet 179 may be arranged in abutting engagement with the plunger rod 177 so as to engage the plunger rod 177 for causing the plunger 129 to move in the longitudinal direction 141, the plunger rod 177 being in abutting engagement with the plunger 129. In some embodiments a plurality of plunger rod magnets 179 may be provided, for example spaced apart from each other along a longitudinal length of the plunger rod 177 in the longitudinal direction 141.

In some embodiments, a plunger bias 165 may be provided. The plunger bias may in some embodiments comprise a compression spring 165. The plunger bias 165 is configured to bias the plunger 129 in distal direction for driving longitudinal movement of the plunger 129 in a distal direction. In some embodiments, the component 130 may be the plunger bias 165. For example, the plunger bias 165 may be a ferromagnetic plunger bias 165 in that the ferromagnetic plunger bias 165 may be made from or may comprise ferromagnetic material. Thus, the ferromagnetic plunger bias 165 may be configured magnetically interact with the magnetic field provided by the plunger drive magnet 133 for causing a force to be applied to the plunger 129 for moving the plunger 129 in the longitudinal direction 141.

FIG. 2A shows the plunger 129 in a first longitudinal position and FIG. 2B shows the plunger 129 in a second longitudinal position in which the plunger has been moved longitudinally in a distal direction compared to FIG. 2A as a result of the force provided by the magnetic interaction of the magnetic field provided by the plunger drive magnet 133 and the component 130.

The plunger drive magnet 133 of the present disclosure may serve to increase the plunger drive force applied to the plunger 129 by virtue of the plunger bias 165 alone. Thus, the plunger drive magnet 133 may supplement or boost the plunger drive force. Thus, a smaller, more compact medicament delivery device 100 may be provided as a smaller, less stiff compression spring 165 may be required. Thus, medicament delivery devices according to the present disclosure advantageously experience less creep, e.g. plastic creep, in the materials of the device 100, for example in the housing 161, for example during storage of the device prior to use. Additionally, the medicament delivery devices 100 of the present disclosure are able to dispense medicament requiring a greater force to be applied to the plunger 129 in order from them to be dispensed, for example medicant having a high viscosity. Therefore, a more versatile medicament delivery device is provided which is capable of dispensing a wider range of medicaments or which is capable of dispensing medicament at a wider range of temperatures.

In some embodiments, the plunger bias 165 may be omitted and the plunger drive magnet 133 may provide the sole plunger driving force.

The medicament delivery device 100 further comprises a needle shield 149 at a distal end of the housing 161. The needle shield 149 is moveable in a longitudinal direction 141 between an extended position (shown in FIG. 2A) and a retracted position (shown in FIG. 2B). In the extended position, the needle shield 149 is arranged to cover the needle 127 of the medicament container 125 when the medicament container 125 is received within the housing 161, for example the needle shield 149 may be arranged to extend distally beyond a distal-most end or tip of the needle 127, as shown in FIG. 2A. In the extended position, the needle shield 149 may prevent stick injuries. The needle shield 149 is configured to move in a proximal direction from the extended position to the retracted position thus, in the retracted position, the needle shield 139 is arranged further proximally than in the extended position such that the needle 127 is exposed for injection. The needle shield is biased in a distal direction towards the extended position by a needle shield extension force, which in this embodiment is provided by a needle shield bias 159 (in this embodiment provided as a compression spring 159) arranged in abutting engagement with the needle shield 139, although any other suitable means of providing the needle shield extension force may instead be provided.

A needle shield retraction magnet 155 is operatively coupled or affixed to the housing 161. As shown in FIGS. 2A and 2B, the needle shield retraction magnet 155 of this embodiment is provided as a ring configured to extend circumferentially around the needle shield 139 such that the needle shield 139 is configured to be received within the annulus of the ring, although this is not essential and any suitable shape or configuration of the needle shield retraction magnet 155 may instead be used. In some embodiments a plurality of such needle shield retraction magnets 155 may be provided.

The needle shield retraction magnet 155 in this embodiment is a permanent magnet. In this embodiment the needle shield retraction magnet 155 is made from a ferromagnetic material although any other suitable magnetic material may instead be used. In other embodiments, such as those disclosed in respect of FIGS. 3A and 3B, the needle shield retraction magnet 155 may be an electromagnet.

The needle shield retraction magnet 155 provides a magnetic field. In this embodiment, the magnetic field of the needle shield retraction magnet 155 is configured to magnetically interact with a component 154 of the medicament delivery device 100 so as to exert a force on the component 154 acting in a proximal direction so as to reduce the needle shield extension force. Thus, the force exerted on the component 154 acts in opposition to the force provided by the needle shield bias 159. In some embodiments, the force exerted on the component 154 causes the needle shield 139 to be retained in the retracted position against the biasing force provided by the needle shield bias 159 when the needle shield 139 is in the retraced position, thereby overcoming the biasing force provided by the needle shield bias 155. Thus, the interaction between the needle shield retraction magnet 155 and the component 154 reduces the holding force required to be applied by a user in order to maintain the needle shield 139 in the retracted position while the device 100 is held at an injection site.

In some embodiments, the component 154 may be the needle shield bias 159 itself. For example, the needle shield bias 159 may be a ferromagnetic needle shield bias 159 comprising or made from a ferromagnetic material. Thus, the needle shield retraction magnet 155 is configured to provide a magnetic field which magnetically interacts with the ferromagnetic needle shield bias 159 so as to exert a force on the needle shield bias 159 acting in a proximal direction so as to act in opposition to the needle shield biasing force provided by the needle shield bias 159, thereby reducing the needle shield extension force and thereby reducing the force required to be applied by a user to move the needle shield 149 to the retracted position against the needle shield extension force and to hold the needle shield 149 in the retracted position as the medicament is delivered.

In some embodiments, the component 154 may be the needle shield 149 itself. For example, the needle shield 149 may be a ferromagnetic needle shield 149 comprising or made from a ferromagnetic material. Thus, the needle shield retraction magnet 155 is configured to provide a magnetic field which magnetically interacts with the ferromagnetic needle shield 149 so as to exert a force on the needle shield 149 acting in a proximal direction so as to act in opposition to the needle shield biasing force provided by the needle shield bias 159, thereby reducing the needle shield extension force and thereby reducing the force required to be applied by a user to move the needle shield 149 to the retracted position against the needle shield extension force and to hold the needle shield 149 in the retracted position as the medicament is delivered.

In some embodiments, the component 154 may be a needle shield magnet 153 operatively coupled, e.g. affixed, to the needle shield 149. In this embodiment the needle shield magnet 153 is a permanent magnet. The needle shield magnet 153 is configured to provide a magnetic field which is configured to magnetically interact with the magnetic field provided by the needle shield retraction magnet 155. The magnetic interaction between the magnetic field provided by the needle shield retraction magnet 155 and the needle shield magnet 153 causes a force to be exerted on the needle shield 149 acting in a proximal direction so as to act in opposition to the needle shield biasing force provided by the needle shield bias 159, thereby reducing the needle shield extension force and thereby reducing the force required to be applied by a user to move the needle shield 149 to the retracted position against the needle shield extension force and to hold the needle shield 149 in the retracted position as the medicament is delivered.

In this embodiment, the needle shield magnet 153 is provided as an insert 153 affixed, e.g. adhered, to the needle shield 149. As shown in FIGS. 2A and 2B, the needle shield magnet 153 of this embodiment is provided as a ring 153 configured to extend circumferentially around the needle shield 149, although this is not essential and any suitable shape or configuration of needle shield magnet 153 may instead be used. In some embodiments a plurality of such needle shield magnets 153 may be provided.

FIG. 2A shows the needle shield 139 in the extended position and FIG. 2B shows the needle shield 139 having been moved to the retracted position (for example by way of a user depressing the needle shield 139 against an injection site).

In some embodiments the plunger drive magnet 133 and the needle shield magnet 155 may be a single, common magnet. Thus, the component 130 and the component 154 may both interact with a single magnetic field provided by the same magnet 133, 155 so as to cause the longitudinal movement of the plunger 129 and also so as to cause the needle shield extension force to be reduced. In order words, the plunger drive magnet 133 may provide a magnetic field which magnetically interacts with the component 154 so as to cause the needle shield extension force to be reduced, thereby reduce the hold force required to be applied by a user in order for a user to hold the device against an injection site, maintaining the needle shield in the retracted position, as the medicament is delivered.

In some embodiments, the medicament delivery device 100 comprises a magnetic field sensor 147. The magnetic field sensor 147 to provide a signal associated with the component 130, for example indicative of the longitudinal position or rate of movement of the component or plunger 129 within the housing 161. For example, the signal may in some embodiments be associated with the magnetic field, or magnetic field intensity, of the component 130, for example of the plunger magnet 131. Thus, the magnetic field sensor 147 may provide a signal indicative of the position of the component 130 and thereby of the longitudinal position of the plunger 129 within the housing 161, or a signal indicative of rate of movement of the component 130 or plunger 129 within the housing 161. In some embodiments, the magnetic field sensor 147 may be a Hall Effect sensor.

In some embodiments, the medicament delivery device 100 may comprises a processor 146, such as a microprocessor. The processor 146 in some embodiments is configured to determine the longitudinal position of the plunger 129 (for example with respect to the medicament container 125 or with respect to the housing 161), a rate of longitudinal movement (e.g. the longitudinal speed or velocity of) of the plunger 129 (for example with respect to the medicament container 125 or with respect to the housing 161), a rate at which medicament is dispensed from the medicament container 125, and/or a quantity of medicament dispensed from the medicament container 125, based on the signal provided by the magnetic field sensor. In some embodiments, the controller 145 may be configured to determine a rate at which medicament is dispensed from the medicament container 125, or a quantity of medicament dispensed from the medicament container 125, based on the determined longitudinal position of the plunger 129 and/or rate of longitudinal movement of the plunger 129.

In some embodiments, the medicament delivery device 100 may comprise an electrical energy source 143 configured to provide power to the processor and/or the controller 145, such as a battery or cell.

In some embodiments, the medicament delivery device 100 comprise a module 163 configured to be detachably attachable to the housing 161, for example by one or more clips (not shown) or by any other suitable alternative means for detachably attaching the module 163 to the housing 161. In the embodiment shown, the module 163 is configured to be detachably attachable to the outside of the housing 161 such that the module 163 may be removable by a user for attaching to the module 163 to another medicament delivery device after the medicament delivery device 100 has been used (e.g. after medicament 126 has been dispensed from the medicament container 125). Thus, the module 163 is transferable between different medicament delivery devices.

In operation, the device 100 of the embodiment of FIGS. 2A and 2B is placed by a user at an injection site. The needle shield 149 is depressed by the user against the injection site such that the needle shield 149 is caused to move from the extended position towards the retracted position. Movement of the needle shield 149 towards the retracted position causes the magnetic field provided by the needle shield retraction magnet 155 to magnetically interact with the component 154 (i.e. the needle shield itself 149, the needle shield bias 159 or the needle shield magnet 153) so as to cause a force to be exerted on the component 154 acting in the proximal direction so as to act in opposition to the biasing force provided by the needle shield bias 159. Thus the magnetic interaction of the magnetic field provided by the needle shield retraction magnet 155 causes a reduction in the needle shield extension force and therefore the force required to maintain the needle shield 149 in the retracted position (i.e. the holding force) is reduced.

A dispensing mechanism (not shown) is triggered by a user so as to cause the plunger 129 to be released for distal movement. As a result of the interaction of the magnetic field of the plunger drive magnet 133 with the component 130 (i.e. the plunger rod 177, the plunger rod magnet 179, the plunger 129, the plunger magnet 131 or the plunger bias 165), a force is exerted on the plunger 129 so as to cause the plunger 129 to move distally. As the plunger 129 moves distally, medicament is caused to be dispense from the medicament container 125 via needle 127.

Figures 3A, 3B:
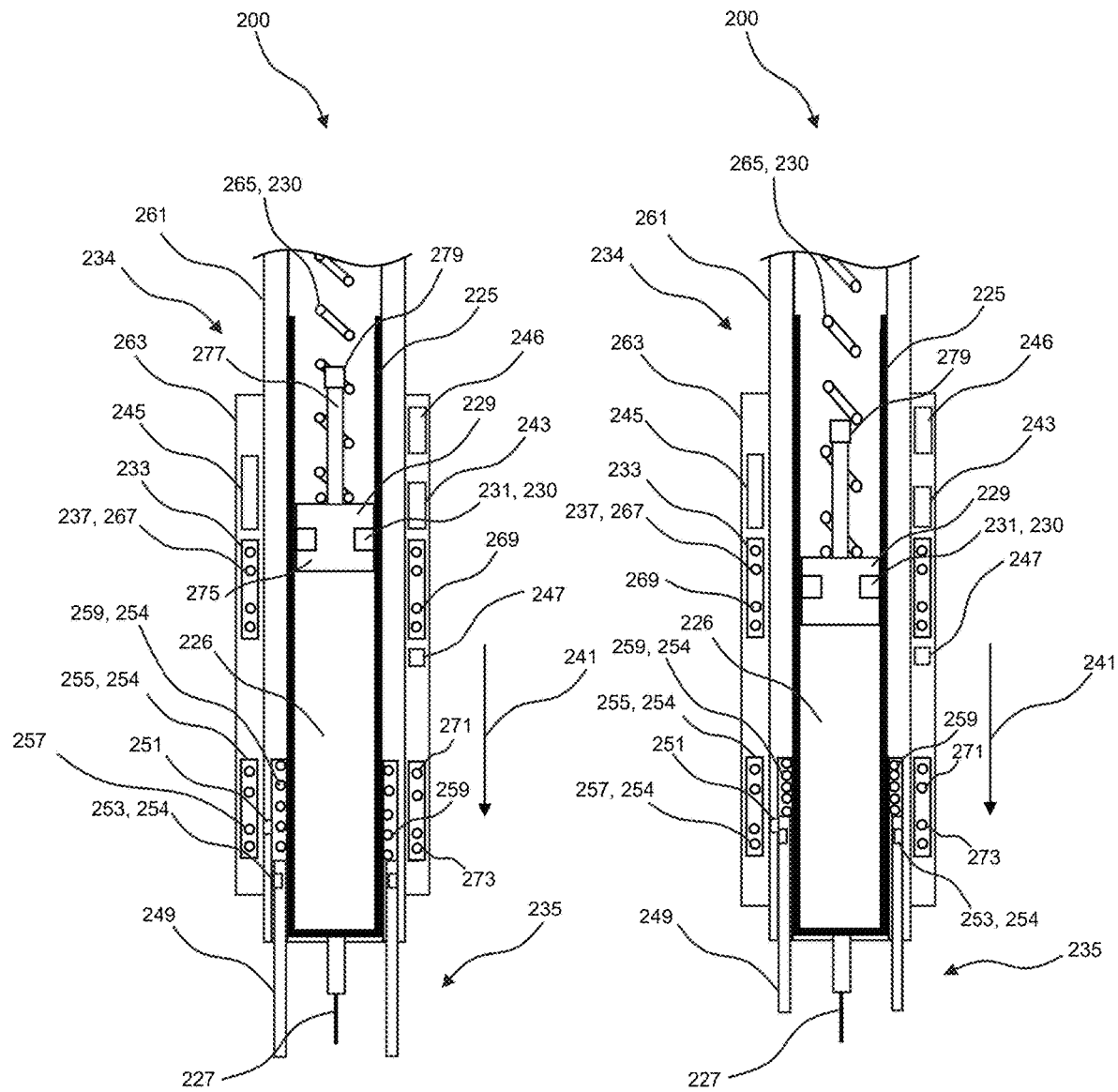
FIG. 3A is a schematic cross-sectional view of parts of another medicament delivery device, the medicament delivery device comprising a plunger drive magnet and a needle shield retraction magnet each comprising an electromagnet, wherein a needle-shield of the medicament delivery device is in an extended position in which a needle of the medicament delivery device is covered.
FIG. 3B is a schematic cross-sectional view of parts of the medicament delivery device of FIG. 3A wherein the needle-shield is in a retracted position in which the needle is exposed for injection.

FIGS. 3A and 3B show a medicament delivery device 200 according to a further embodiment of the present disclosure. The medicament delivery device 200 of this example is also an autoinjector.

The medicament delivery device 200 shares common features to the medicament delivery device 100 of the embodiments of FIGS. 2A and 2B and so redundant discussion of the medicament delivery device 200 of FIGS. 3A and 3B will be omitted for the sake of brevity. Features of the medicament delivery device 200 of FIGS. 3A and 3B corresponding to features of the medicament delivery device 100 of FIGS. 2A and 2B share corresponding reference numerals, with those of the medicament delivery device 200 of FIGS. 3A and 3B being increased by 100.

Compared to the medicament delivery device 100 of FIGS. 2A and 2B, a difference of the medicament delivery device 200 of FIGS. 3A and 3B is that the plunger drive magnet 233 and the needle shield retraction magnet 255 each comprise an electromagnet, rather than a permanent magnet, and that the medicament delivery device 200 further comprises a switch 251 and a controller 245. In other embodiments, one of the plunger drive magnet 233 and the needle shield retraction magnet 255 may comprise a permanent magnet and the other one may comprise an electromagnet.

The electromagnet of the plunger drive magnet 233 comprises an energizable coil 237. The energizable coil 237 is energizable so as to provide a magnetic field. The energizable coil 237 may comprise a coil, or winding, of conductive material, such as an electrically conductive wire, for example a copper wire. The energizable coil 237 of the plunger drive magnet 233 is arranged to extend, or wind, peripherally around the medicament container 225 such that the medicament container 225 is received within an annulus defined by the energizable coil 237. In the embodiment shown, the energizable coil 237 is a first energizable coil 267 and the plunger drive magnet 233 further comprises and second energizable coil 269 spaced apart from the first energizable coil 267 in a longitudinal direction 241 of the device 200. The first 267 and second 269 energizable coils may in some embodiments be independently energizable.

Similarly, the electromagnet of the needle retraction magnet 255 comprises an energizable coil 257. The energizable coil 257 is energizable so as to provide a magnetic field. The energizable coil 257 may comprise a coil, or winding, of conductive material, such as an electrically conductive wire, for example a copper wire. In some embodiments, the energizable coil 257 of the needle retraction magnet 255 may be arranged to extend, or wind, peripherally around the needle shield 249 such that the needle shield 249 is received within an annulus defined by the energizable coil 257 in the retracted position. In the embodiment shown, the energizable coil 257 comprises a first energizable coil 271 and the needle shield retraction magnet 235 comprises a second energizable coil 273 spaced apart from the first energizable coil 271 in a longitudinal direction 241 of the device 200. The first 271 and second 273 energizable coils may in some embodiments be independently energizable.

A controller 245 is configured to control the electromagnet of the plunger drive magnet 233 so as to control the magnetic field (e.g. an intensity thereof) provided by the electromagnet of the plunger drive magnet 233 and thereby control the force exerted on the plunger 229 so as to thereby control the longitudinal movement of the plunger 229 with respect to the medicament container 225 or housing 261.

In some embodiments, the controller 245 is configured to control the electromagnet of the plunger drive magnet 233 so as to control the longitudinal movement of, or force exerted on, the plunger 229 based on the determined longitudinal position of the plunger 229, for example with respect to the medicament container 225 or housing 261, the determined rate of longitudinal movement (i.e. the speed or rate of advancement) of the plunger 229, for example with respect to the medicament container 225 or housing 261, the determined rate at which medicament 226 is dispensed from the medicament container 225, and/or the determined quantity of medicament 226 dispensed from the medicament container 225 as determined by the processor 247 based on a signal received by the processor 247 from the magnetic field sensor 247. Thus, by controlling the longitudinal movement of, or force exerted on, the plunger 229 based on the determined longitudinal position of the plunger 229, for example with respect to the medicament container 225 or housing 261, the determined rate of longitudinal movement (i.e. the speed, velocity or rate of advancement) of the plunger 229, for example with respect to the medicament container 225 or housing 261, and/or the determined rate at which medicament 226 is dispensed from the medicament container 225, the controller 245 may be configured to provide a substantially constant rate of medicament dispensed from the medicament container 225.

In some embodiments, the controller 245 is configured to independently or individually control the energizable coils 267, 269 of the electromagnet of the plunger drive magnet 233. In some embodiments, the controller 245 may be configured to independently or individually control the energizable coils 267, 269 of the electromagnet of the plunger drive magnet 233 so as to control the longitudinal movement of, or force exerted on, the plunger 229 based on the determined longitudinal position of the plunger 229, for example with respect to the medicament container 225 or housing 261, the determined rate of longitudinal movement (i.e. the speed. velocity or rate of advancement) of the plunger 229, for example with respect to the medicament container 225 or housing 261, the determined rate at which medicament 226 is dispensed from the medicament container 225, and/or the determined quantity of medicament 226 dispensed from the medicament container 225.

In some embodiments, the controller 245 is configured to selectively energize one or more of the plurality of energizable coils 267, 269 of the electromagnet of the plunger drive magnet 233, and thereby the force exerted on the plunger 229, based on the determined longitudinal position of the plunger 229, for example with respect to the medicament container 225 or housing 261, the determined rate of longitudinal movement (i.e. the speed or rate of advancement) of the plunger 229, for example with respect to the medicament container 225 or housing 261, the determined rate at which medicament 226 is dispensed from the medicament container 225, or the determined quantity of medicament 226 dispensed from the medicament container 225. For example, a first one of the energizable coils 267 may first be energised and then a second one of the energizable coils 269 may then be energised in addition or in alternative to the first energizable coil 267.

The controller 245 is also configured to control the electromagnet of the needle shield retraction magnet 255 so as to control the force (e.g. a magnitude thereof) exerted on the component 254. In some embodiments, the controller 245 may control the electromagnet of the needle shield retraction magnet 255, and thereby the force exerted on the component 254, based on the determined longitudinal position of the plunger 229 within the housing 261, the determined rate of movement of the plunger 229 in the longitudinal direction within the housing 261, the determined rate at which medicament is dispensed from the medicament container 225, and/or the determined quantity of medicament dispensed from the medicament container 225.

In some embodiments, the controller 245 is configured to independently or individually control the first and second energizable coils 271, 273 of the electromagnet of the needle shield retraction magnet 255. The module 263 may in some embodiments comprise the controller 245.

The electrical energy source 243 is configured to provide electrical power to the electromagnet of the plunger drive magnet 233 and the needle shield retraction magnet 255 for energising them so as to provide their respective magnetic fields. For example the controller may control the flow (e.g. rate of flow) of electrical energy from the electrical energy source 243 to the electromagnet of the plunger drive magnet 233 and/or the needle shield retraction magnet 255.

The switch 251 is configured to actuate upon movement of the needle shield from the extended position towards (or in some embodiments to) the retracted position. In some embodiments, the switch 251 is configured to energise the electromagnet of the plunger drive magnet 233 and the needle shield retraction magnet 255 upon movement of the needle shield from the extended position towards the retracted position. In some embodiments, the switch 251 is configured to provide electrical power to the processor and/or controller upon movement of the needle shield from the extended position towards the retracted position. The module 263 may in some embodiments comprise the switch 251.

In operation, the device 200 of the embodiment of FIGS. 3A and 3B is placed by a user at an injection site. The needle shield 249 is depressed by the user against the injection site such that the needle shield 249 is caused to move from the extended position towards the retracted position, against the needle shield extension force, causing switch 251 to be actuated. Actuation of the switch 251 causes electrical power to be supplied to the processor 246 and the controller 245 from the electrical energy source 143.

The processor 246 then (e.g. continuously) determines one or more of a longitudinal position of the plunger 229 within the housing 261, a rate of movement of the plunger in the longitudinal direction within the housing, a rate at which medicament 226 is dispensed from the medicament container 225, and/or a quantity of medicament dispensed from the medicament container 225, based on the signal provided by the magnetic field sensor 247.

At the same time, the controller 245 energises the electromagnet of the plunger drive magnet 233 and/or of the needle shield retraction magnet 255 so as to provide a magnetic field of the plunger drive magnet 233 and a magnetic field of the shield retraction magnet 255 respectively.

The interaction of the magnetic field of the plunger magnet 231 with the magnetic field of the component 230 causes a force to be exerted on the plunger 229 which causes the plunger 229 to move in a distal direction within the medicament container 225 so as to cause medicament 226 to be dispensed from the medicament container 225 via the needle 227. The controller 245 then (e.g. continuously) controls the electromagnet of the plunger drive magnet 233 so as to control the force exerted on the plunger 229, or the longitudinal position of the plunger 229 within the housing 261, based on the determined one or more of a longitudinal position of the plunger 229 within the housing 261, a rate of movement of the plunger in the longitudinal direction within the housing, rate at which medicament 226 is dispensed from the medicament container 225, and/or a quantity of medicament dispensed from the medicament container 225. In some embodiments, the controller 245 is configured to control the electromagnet of the plunger drive magnet 233 so as to provide a constant rate at which medicament 226 is dispensed from the medicament container 225. In other embodiments, the controller 245 is configured to control the electromagnet of the plunger drive magnet 233 so as to control the movement of the plunger 229 (e.g. the longitudinal position of the plunger 229 within the housing 261) so as to provide a predetermined quantity of medicament 226 dispensed from the medicament container 225.

The interaction of the magnetic field of the magnetic field of the needle shield retraction magnet 255 with the component 254 (i.e. with the needle shield bias 255, the needle shield 249 or the needle shield magnet 253) causes a force to be exerted on the component 254 acting in a direction towards the retracted position. This force acts in opposition to the biasing force provided by the needle shield bias 259 and thus reduces the needle shield extension force and thereby the hold force required to be applied by the user in order to hold the needle shield 249 in the retracted position when depressing the device 200 against an injection site. The controller 245 then controls the electromagnet of the needle shield retraction magnet 255 so as to control the force exerted on the component 254 based on the determined one or more of a longitudinal position of the plunger 229 within the housing 261, a rate of movement of the plunger in the longitudinal direction within the housing, a rate at which medicament 226 is dispensed from the medicament container 225, and/or a quantity of medicament dispensed from the medicament container 225. In some embodiments, the controller 245 controls the electromagnet of the needle shield retraction magnet 255 based on the longitudinal position of the plunger 229 within the housing 261. In some embodiments, the controller may be configured to control the electromagnet of the needle shield retraction magnet 255 so as to reduce the magnetic force acting on component 254 when the processor determines that the plunger 229 is at a predetermined longitudinal position (for example indicative of a pre-determined dose of medicament having been dispensed) or when the processor determines that a predetermined dose of medicament has been dispensed or when a predetermined period of time has passed, thereby increasing the needle shield extension force and thereby increasing the hold force.

The dispensing mechanism provides one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety medicament container, pen-injector, or auto-injector. For example, a delivery device could include a mechanical energy source configured to automatically inject a medicament (as typically found in an auto-injector) and a dose setting mechanism (as typically found in a pen-injector).

The medicament delivery device can include various types of safety medicament container, pen-injector, or auto-injector. The device can include a cartridge-based system that requires piercing a sealed ampule before use.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, medicament container, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs)

separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merc.

Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codeable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly (A21), Arg (B31), Arg (B32) human insulin (insulin glargine); Lys (B3), Glu (B29) human insulin (insulin glulisine); Lys (B28), Pro (B29) human insulin (insulin lispro); Asp (B28) human insulin (insulin aspart); human insulin, wherein proline in position B28 is replaced by Asp, Lys, Leu, Val or Ala and wherein in position B29 Lys may be replaced by Pro; Ala (B26) human insulin; Des (B28-B30) human insulin; Des (B27) human insulin and Des (B30) human insulin.

Examples of insulin derivatives are, for example, B29-N-myristoyl-des (B30) human insulin, Lys (B29) (N-tetradecanoyl)-des (B30) human insulin (insulin detemir, Levemir®); B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des (B30) human insulin, B29-N-omega-carboxypentadecanoyl-gamma-L-glutamyl-des (B30) human insulin (insulin degludec, Tresiba®); B29-N-(N-lithocholyl-gamma-glutamyl)-des (B30) human insulin; B29-N-(ω-carboxyheptadecanoyl)-des (B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091 MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrom.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to magnetically interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1:2014(E). As described in ISO 11608-1:2014(E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

LIST OF FEATURES

10—Device
11—housing
12—cap
13—needle sleeve
17—needle
20—distal region
21—proximal region
22—button
23—piston
100—medicament delivery device
125—medicament container
126—medicament
127—needle
129—plunger
130—component
131—plunger magnet
133—plunger drive magnet
134—proximal end
135—distal end
139—plurality of energizable coils
141—longitudinal direction of the housing
143—electrical energy source
146—processor
147—magnetic field sensor
149—needle shield
153—needle shield magnet
154—component
155—needle shield retraction magnet
159—needle shield bias
161—housing of the device
163—module
165—plunger bias
175—piston
177—plunger rod
179—plunger rod magnet
200—medicament delivery device
225—medicament container
226—medicament
227—needle
229—plunger
231—plunger magnet
233—plunger drive magnet
234—proximal end
235—distal end
237—energizable coil
241—longitudinal direction of the housing 243—electrical energy source
245—controller
246—processor
247—magnetic field sensor
249—needle shield
251—switch
253—needle shield magnet
254—component
255—needle shield retraction magnet
257—energizable coil
259—needle shield bias
261—housing of the device
263—module
265—plunger bias
267—first energizable coil of plunger drive magnet
269—second energizable coil of plunger drive magnet
271—first energizable coil of needle shield retraction magnet
273—second energizable coil of needle shield retraction magnet
275—piston
277—plunger rod
279—plunger rod magnet

The invention claimed is:

1. A medicament delivery device for injecting medicament, wherein the medicament delivery device comprises:
    a housing having a proximal end and a distal end, the housing being configured to receive a medicament container;
    a needle shield configured to be movable between an extended position for covering a needle of the medicament container when the medicament container is received within the housing and a retracted position for exposing the needle for an injection;
    a plunger moveable in a longitudinal direction within the housing for dispensing medicament from the medicament container when the medicament container is received within the housing;
    a plunger drive magnet operatively coupled to the housing, the plunger drive magnet being configured to provide a magnetic field; and
    a component configured to magnetically interact with the magnetic field of the plunger drive magnet to cause a force to be exerted on the plunger for causing the plunger to move in the longitudinal direction.

2. The medicament delivery device according to claim 1, wherein the component is a plunger bias configured to bias the plunger in the longitudinal direction.

3. The medicament delivery device according to claim 1, wherein the component is a plunger magnet operatively coupled to the plunger, wherein the plunger magnet is configured to provide a magnetic field configured to magnetically interact with the magnetic field of the plunger drive magnet so as to cause the force to be exerted on the plunger for causing the plunger to move in the longitudinal direction.

4. The medicament delivery device according to claim 1, wherein the medicament delivery device comprises a plunger rod and wherein the component is a plunger rod magnet operatively coupled to the plunger rod, wherein the plunger rod magnet is configured to provide a magnetic field configured to magnetically interact with the magnetic field of the plunger drive magnet so as to cause the force to be exerted on the plunger for causing the plunger to move in the longitudinal direction.

5. The medicament delivery device according to claim 1, wherein the plunger drive magnet comprises an electromagnet.

6. The medicament delivery device according to claim 5, wherein the medicament delivery device comprises a controller configured to control the electromagnet of the plunger drive magnet so as to control the force exerted on the plunger.

7. The medicament delivery device according to claim 6, wherein the controller is configured to control the electromagnet of the plunger drive magnet so as to control a rate of movement of the plunger in the longitudinal direction.

8. The medicament delivery device according to claim 7, wherein the medicament delivery device comprises a magnetic field sensor configured to provide a signal associated with the component.

9. The medicament delivery device according to claim 8, wherein the medicament delivery device comprises a processor configured to determine one or more of a longitudinal position of the plunger within the housing, a rate of movement of the plunger in the longitudinal direction within the housing, a rate at which medicament is dispensed from the medicament container, or a quantity of medicament dispensed from the medicament container, based on the signal provided by the magnetic field sensor.

10. The medicament delivery device according to claim 9, wherein the controller is configured to control the electromagnet of the plunger drive magnet so as to control the force exerted on the plunger based on the longitudinal position of the plunger within the housing, the rate of movement of the plunger in the longitudinal direction within the housing, the rate at which medicament is dispensed from the medicament container, or the quantity of medicament dispensed from the medicament container.

11. The medicament delivery device according to claim 1, wherein the plunger drive magnet comprises an electromagnet and wherein the medicament delivery device comprises a switch configured to energize the electromagnet of the plunger drive magnet so as to provide the magnetic field of the plunger drive magnet upon movement of the needle shield from the extended position towards the retracted position.

12. The medicament delivery device according to claim 1, wherein the medicament container contains medicament.

13. A method of using a medicament delivery device for injecting medicament, the medicament delivery device comprising:
    a housing having a proximal end and a distal end, the housing being configured to receive a medicament container;
    a needle shield configured to be movable between an extended position for covering a needle of the medicament container when the medicament container is received within the housing and a retracted position for exposing the needle for an injection;
    a plunger moveable in a longitudinal direction within the housing for dispensing medicament from the medicament container when the medicament container is received within the housing;
    a plunger drive magnet operatively coupled to the housing, the plunger drive magnet being configured to provide a magnetic field; and
    a component configured to magnetically interact with the magnetic field of the plunger drive magnet;
    wherein the method comprises:
        causing the component to magnetically interact with the magnetic field of the plunger drive magnet to cause a force to be exerted on the plunger for causing the plunger to move in the longitudinal direction.

14. The method of claim 13, wherein the plunger drive magnet comprises an electromagnet, wherein the medicament delivery device comprises:
- a switch configured to energize the electromagnet of the plunger drive magnet so as to provide the magnetic field of the plunger drive magnet upon movement of the needle shield from the extended position towards the retracted position;
- wherein the method comprises:
  - moving the needle shield from the extended position towards the retracted position so as to actuate the switch to thereby cause the electromagnet of the plunger drive magnet to become energized so as to provide the magnetic field of the plunger drive magnet and thereby cause the force to be exerted on the plunger for causing the plunger to move in the longitudinal direction.

15. The method of claim 13, wherein the plunger drive magnet comprises an electromagnet, the medicament delivery device comprising a controller configured to control the electromagnet of the plunger drive magnet so as to control the force exerted on the plunger;
- wherein the method further comprises:
  - controlling the electromagnet of the plunger drive magnet so as to control the force exerted on the plunger.

16. The method of claim 15, wherein the medicament delivery device comprises:
- a magnetic field sensor configured to provide a signal associated with the component;
- a processor configured to determine one or more of a longitudinal position of the plunger within the housing, a rate of movement of the plunger in the longitudinal direction within the housing, a rate at which medicament is dispensed from the medicament container, or a quantity of medicament dispensed from the medicament container, based on the signal provided by the magnetic field sensor; and
- a controller configured to control the electromagnet of the plunger drive magnet so as to control the force exerted on the plunger based on the longitudinal position of the plunger within the housing, the rate of movement of the plunger within the housing in the longitudinal direction, the rate at which medicament is dispensed from the medicament container, or the quantity of medicament dispensed from the medicament container, and
- wherein the method further comprises:
- receiving a signal associated with the component from the magnetic field sensor;
- determining one or more of the longitudinal position of the plunger within the housing, the rate of movement of the plunger in the longitudinal direction within the housing, the rate at which medicament is dispensed from the medicament container, or the quantity of medicament dispensed from the medicament container, based on the received signal; and
- controlling the electromagnet of the plunger drive magnet based on the longitudinal position of the plunger within the housing, the rate of movement of the plunger in the longitudinal direction within the housing, the rate at which medicament is dispensed from the medicament container, or the quantity of medicament dispensed from the medicament container so as to control the force exerted on the plunger.

17. A medicament delivery device for injecting medicament, wherein the medicament delivery device comprises:
- a housing having a proximal end and a distal end, the housing being configured to receive a medicament container comprising a needle;
- a needle shield configured to be movable between an extended position for covering the needle of the medicament container when the medicament container is received within the housing and a retracted position for exposing the needle for injection, the needle shield being configured to be movable in a proximal direction of the housing from the extended position to the retracted position, the needle shield being biased in a distal direction towards the extended position by a needle shield extension force;
- a needle shield retraction magnet operatively coupled to the housing, the needle shield retraction magnet being configured to provide a magnetic field; and
- a component configured to magnetically interact with the magnetic field of the needle shield retraction magnet so as to cause a force to be exerted on the component, the force acting in a proximal direction so as to reduce the needle shield extension force.

18. A method of using a medicament delivery device for injecting medicament, the medicament delivery device comprising:
- a housing having a proximal end and a distal end, the housing being configured to receive a medicament container comprising a needle;
- a needle shield configured to be movable between an extended position for covering the needle of the medicament container when the medicament container is received within the housing and a retracted position for exposing the needle for injection, the needle shield being configured to be movable in a proximal direction of the housing from the extended position to the retracted position, the needle shield being biased in a distal direction towards the extended position by a needle shield extension force;
- a needle shield retraction magnet operatively coupled to the housing, the needle shield retraction magnet being configured to provide a magnetic field; and
- a component configured to magnetically interact with the magnetic field of the needle shield retraction magnet, and
- wherein the method comprises:
  - causing the component to magnetically interact with the magnetic field of the needle shield retraction magnet so as to cause a force to be exerted on the component, the force acting in a proximal direction so as to reduce the needle shield extension force.

19. The method of claim 18, wherein the needle shield retraction magnet comprises an electromagnet configured to provide the magnetic field of the needle shield retraction magnet and the medicament delivery device further comprises a switch configured to energise the electromagnet of the needle shield retraction magnet so as to provide the magnetic field of the needle shield retraction magnet upon movement of the needle shield from the extended position towards the retracted position;
- wherein the method comprises:
  - moving the needle shield from the extended position towards the retracted position so as to cause the switch to energise the electromagnet of the needle shield retraction magnet so as to provide the magnetic field of the needle shield retraction magnet and thereby cause the force to be exerted on the component, the force acting in a proximal direction so as to reduce the needle shield extension force.

* * * * *